(12) United States Patent
Gatzemeyer et al.

(10) Patent No.: US 8,250,694 B2
(45) Date of Patent: *Aug. 28, 2012

(54) POWERED TOOTHBRUSH WITH ROTATING SECTIONS

(75) Inventors: John J. Gatzemeyer, Hillsborough, NJ (US); Thomas Mintel, Rahway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/107,640

(22) Filed: May 13, 2011

(65) Prior Publication Data

US 2011/0283470 A1  Nov. 24, 2011

Related U.S. Application Data

(62) Division of application No. 12/472,807, filed on May 27, 2009, now Pat. No. 7,954,192, which is a division of application No. 10/107,092, filed on Mar. 26, 2002, now Pat. No. 7,552,497.

(51) Int. Cl.
*A61C 17/34* (2006.01)
(52) U.S. Cl. .............................. 15/22.1; 15/22.2; 15/28
(58) Field of Classification Search ............. 15/22.1, 15/22.2, 28
See application file for complete search history.

(56) References Cited

U.S. PATENT DOCUMENTS

| 1,796,641 | A | 3/1928 | Zimmerman et al. |
| 5,070,567 | A | 12/1991 | Holland |
| 5,259,083 | A | 11/1993 | Stansbury, Jr. |
| 5,416,942 | A | 5/1995 | Baldacci et al. |
| 5,467,495 | A | 11/1995 | Boland et al. |
| 5,524,312 | A | 6/1996 | Tan et al. |
| 5,577,285 | A | 11/1996 | Drossler |
| 5,625,916 | A | 5/1997 | McDougall |
| 5,732,433 | A | 3/1998 | Gocking et al. |
| 6,000,083 | A | 12/1999 | Blaustein et al. |
| 6,032,313 | A | 3/2000 | Tsang |
| 6,168,241 | B1 | 1/2001 | Zapanta |
| 6,360,395 | B2 | 3/2002 | Blaustein et al. |
| 6,564,416 | B1 | 5/2003 | Claire et al. |
| 6,725,490 | B2 | 4/2004 | Blaustein et al. |
| 6,889,401 | B2 | 5/2005 | Fattori et al. |
| 2003/0033679 | A1 | 2/2003 | Fattori et al. |
| 2003/0163882 | A1 | 9/2003 | Blaustein et al. |

FOREIGN PATENT DOCUMENTS

| EP | 0765642 | 4/1997 |
| EP | 1132022 | 9/2001 |
| EP | 1132057 | 9/2001 |
| WO | 0160281 | 8/2001 |

*Primary Examiner* — Randall Chin
(74) *Attorney, Agent, or Firm* — Amy M. Fernandez

(57) ABSTRACT

The head of a toothbrush includes a first tuft block having bristles and a second tuft block having bristles. The first and second tuft blocks are mounted for counter-rotational or counter-rotational oscillating movement in a direction parallel to the outer surface of the head. The toothbrush head also includes a third section having bristles extending outwardly from the head to provide an extended field of bristles to support an elongated ribbon of toothpaste and for enhanced cleaning.

2 Claims, 4 Drawing Sheets

POWERED TOOTHBRUSH WITH ROTATING SECTIONS

CROSS-REFERENCE TO RELATED APPLICATIONS

The present application is a divisional of U.S. patent application Ser. No. 12/472,807, filed on May 27, 2009, now U.S. Pat. No. 7,954,192, which is a divisional of U.S. patent application Ser No. 10/107,092, filed on Mar. 26, 2002, now U.S. Pat. No. 7,552,497, the contents of each are incorporated herein by reference.

FIELD OF THE INVENTION

The present invention relates to toothbrushes which include rotating sections in the head.

BACKGROUND OF THE INVENTION

The present invention is directed to a powered toothbrush and in particular to a toothbrush head having movably mounted bristles. Various types of powered toothbrushes are generally known in the art. Reference is made to U.S. Pat. No. 5,625,915 which relates to an electrically driven toothbrush having a motor drive for rotating a drive shaft. The drive shaft is connected to a bristle holder on the head of the toothbrush in such a manner that rotation of the drive shaft causes the bristle holder to rotationally oscillate back and forth. Various other arrangements are known for oscillating a bristle holder mounted to the head of an electric toothbrush.

U.S. Pat. No. 5,416,942 shows a further type of powered toothbrush wherein the head includes a pair of concentrically arranged sections, each of which is driven in a rotational oscillating manner in opposite directions. The toothbrush head, however, includes only the two counter-oscillating sections. The head does not include any other sections on which bristles may be mounted.

U.S. Pat. No. 6,032,313 discloses a household appliance which would be used for cleaning, polishing or massaging. One such appliance is a toothbrush. The head has a plurality of co-axially rotatable or parallel linearly movable sections. No provision is made on the head for other bristle containing sections.

U.S. Pat. No. 5,070,567 discloses an electrically driven toothbrush which includes a rotatable brush head having bristles thereon. Adjacent to the brush head are a further group of bristles each of which rotates around its own axis.

U.S. Pat. No. 1,796,641 relates to a spotting brush usable for dry-cleaning wherein a pair of side by side heads are rotatably mounted.

SUMMARY OF THE INVENTION

An object of this invention is to provide a powered toothbrush which includes counter-rotational or oscillating sections and a further section having bristles to deliver a cleaning, polishing, whitening action in addition to enhancing the cleaning efficiency of a typical powered toothbrush.

In accordance with this invention the toothbrush head includes a first section or tuft block which is mounted for oscillating back and forth in a rotational direction parallel to the outer surface of the toothbrush head. A second section or tuft block is mounted for oscillating back and forth in a rotational direction also parallel to the toothbrush head, but in counteroscillation to the direction of the first tuft block. A third section or tuft block is provided on the toothbrush head and also contains bristles.

In various practices of the invention the third section could be a fixed non-moving section wherein the bristles are also fixed. Alternatively, the bristles or the fixed section could be mounted movably in an elastomer material on the section to permit independent movement of such bristles, although the fixed section remains stationary.

In other practices of the invention the third section could be a movable section which oscillates back and forth in a direction parallel to the longitudinal axis of the toothbrush head or in a direction transverse to the longitudinal axis of the toothbrush head. In yet another alternative practice of the invention the third section could oscillate in and out in a direction perpendicular to the outer surface of the toothbrush head to form a vibrating section which vibrating section may or may not simultaneously oscillate back and forth.

In a preferred practice of the invention the second tuft head is mounted within and concentric to the first tuft block. The bristles of the first tuft block may extend outwardly from the outer surface of the head a greater distance than the bristles of the second tuft head so as to create a cup-like shape which would facilitate retaining the toothpaste on the first and second tuft heads.

The third section is preferably mounted longitudinally in line with the first and second sections so that the portion of the head containing the bristles of the first, second and third sections is of an elongated shape which would also facilitate holding an elongated ribbon of toothpaste on the bristles.

THE DRAWINGS

DETAILED DESCRIPTION

FIGS. 1-4 illustrate one practice of this invention wherein a toothbrush 10 includes a neck section 12 of a handle 30, which is partially shown, and includes a head 14. The head 14 may be a replaceable, i.e. a refill head or the head 14 may be permanently attached to the handle 30 within the practice of this invention.

Figure 2:
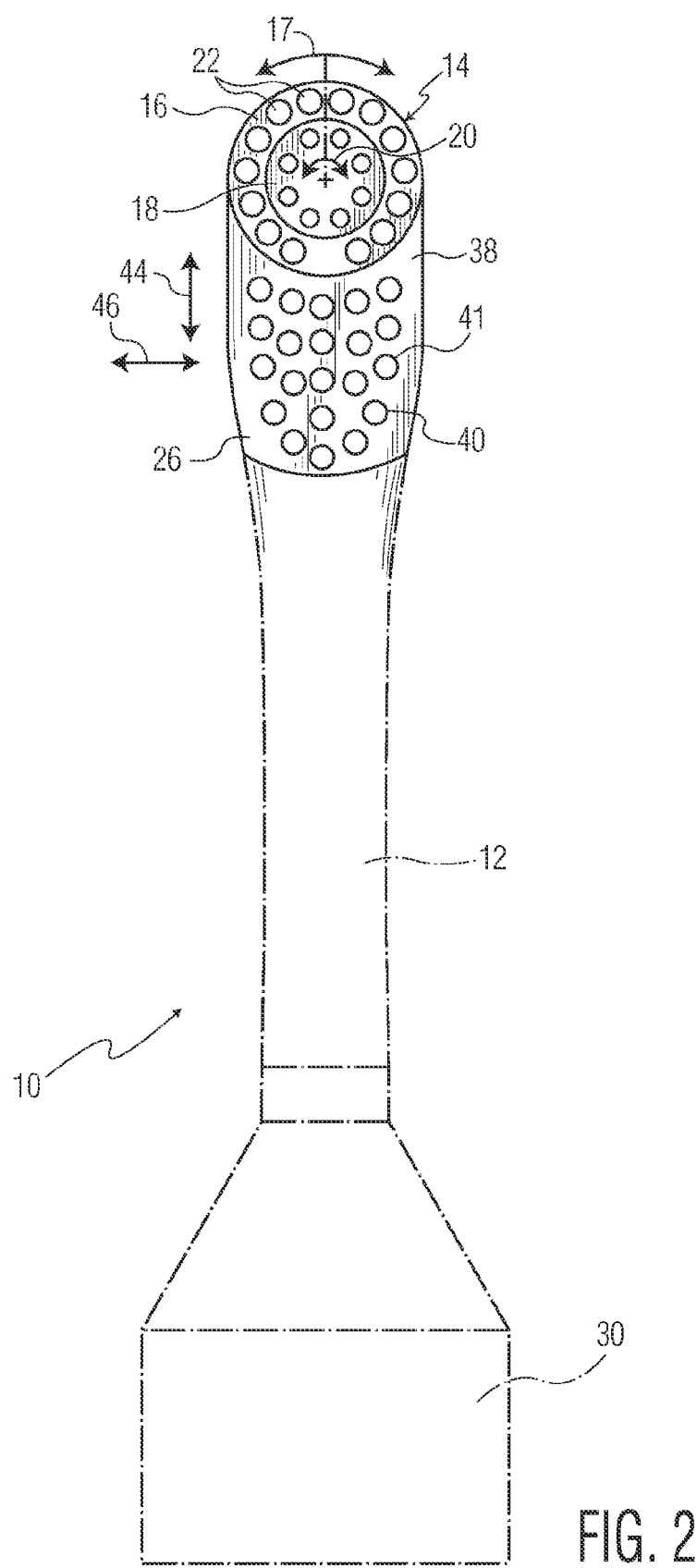
FIG. 2 is a front elevational view of the head shown in FIG. 1.

As illustrated, particularly in FIG. 2, the head 14 includes a first tuft block 16 which is illustrated as being at the outermost or distal portion of head 14. Tuft block 16 is preferably a disk of circular ring type shape having an open inner area. Tuft block 16 is intended to oscillate in a rotational manner as indicated by the arrow 17. If desired, other shapes may be used such as an egg shape or an oval or various regular or irregular shapes, as long as (in the preferred practice of the invention) there is an open area in which a second tuft block 18 may be mounted. An egg shape or circular shape of the tuft block 16 is preferred, with a circular shape being most preferred since such shape requires the least amount of clearance to accommodate the oscillating motion and to accommodate the inner second tuft block 18.

Tuft block 18 is preferably a disk of circular cross-section which is also intended to oscillate in a rotational manner, such as indicated by the arrow 20. Thus, first tuft block 16 and second tuft block 18 are mounted concentric with each other at the distal end of head 14.

First tuft block 16 includes a plurality of tufts of bristles 22. In the illustrated embodiment the tufts of bristles 22 are formed in a coarcuate row. Similarly, tuft block 18 is provided with a plurality of tufts of bristles 24 which may be also coarcuate with each other along a circle parallel to the arcuate row of bristles 22.

Figure 4:
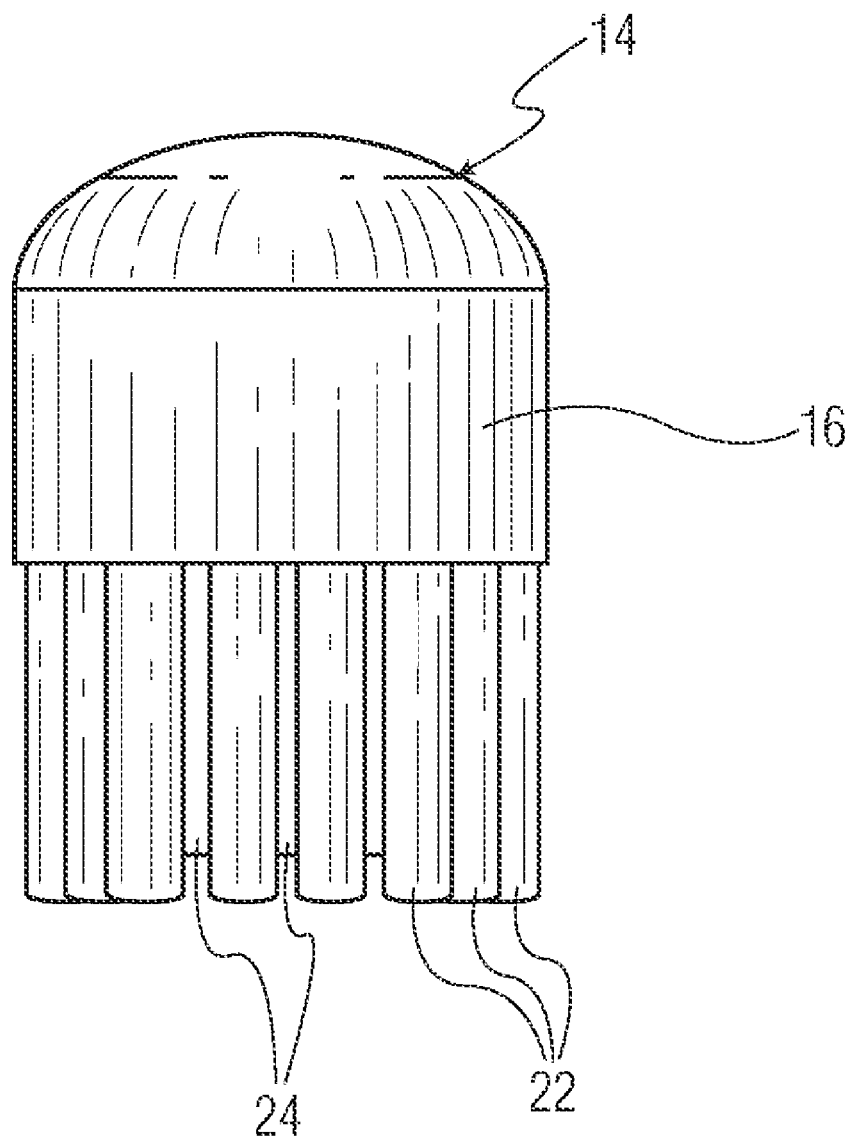
FIG. 4 is a top plan view of the head shown in FIGS. 1-3.

The two coarcuate sets of bristles 22,24 are preferred since such arrangement maximizes bristle density on the surface area of tuft blocks 16 and 18 and if the diameter dimension of the tuft block 18 is sufficient, additional tufts can be located centrally therein. In the preferred practice of the invention the outer row of bristles 22 extend outwardly from the outer surface 26 of head 14 a greater distance than the inner arcuate row of bristles 24. As a result, a cup-like structure is formed which facilitates retaining toothpaste on the bristles 22,24, as shown in FIG. 4. As shown in FIG. 2 the outer row of bristles 22 extend generally perpendicular to the tuft block 16; however, the outer row of bristles 22 can be splayed outwardly from the tuft block 16 at an acute angle thereto.

Figure 3:
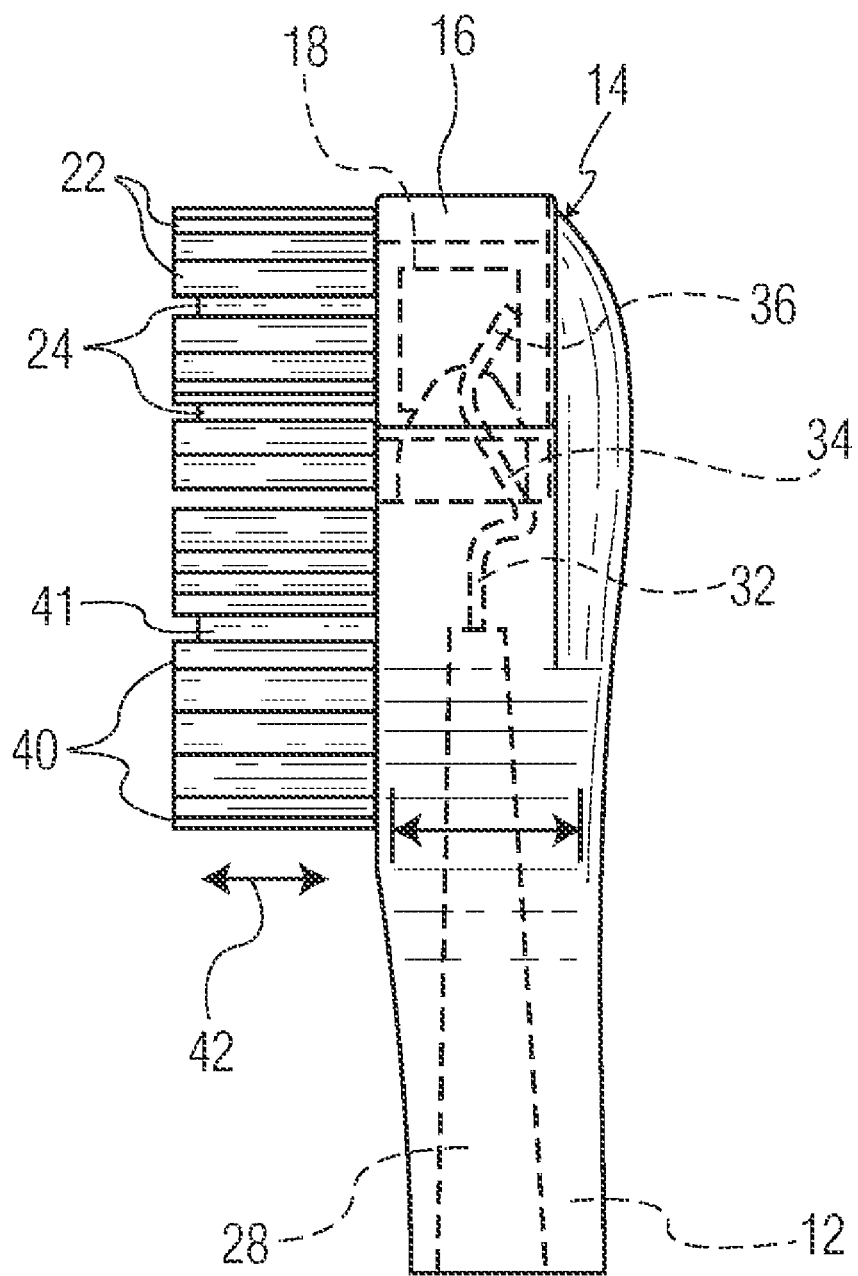
FIG. 3 is a side elevational view of the head shown in FIGS. 1-2.

Tuft blocks 16 and 18 may be oscillated by any suitable drive mechanism. FIG. 3, for example, illustrates the type of drive mechanism described in U.S. Pat. No. 5,146,942, all of the details of which are incorporated herein by reference thereto. As shown therein, a drive shaft 28 is rotated by a driving motor (not shown) in the handle 30. See FIG. 2. The motor could be powered in any suitable manner such as by batteries. As shown in FIG. 3, a transmission spindle 32 is operatively connected such as by a permanent or detachable conreaction to drive shaft 28. Spindle 32 has a V-segment oriented perpendicularly to the axis of rotation of the drive shaft 28 and eccentrically with respect to the axis of rotation. A first inclined arm 34 engages in an axial slot in first tuft block 16. A second distal arm 36 engages in an axial slot in second tuft block 18. Rotation of shaft 28 and spindle 32 results in rotation of arms 34,36. Because the eccentric portions of arms 34,36 are mounted in slots in tuft blocks 16,18 the rotational movement is transmitted to the tuft blocks as an oscillating rotational movement shown by the arrows 17 and 20 of FIG. 2. As driven by the spindle 32, the rotational movement of first tuft block 16 will be opposite in direction from that of second tuft block 18.

In the preferred practice of this invention the counteroscillating first and second tuft blocks are mounted concentric to each other as illustrated. It is to be understood, however, that the invention may also be practiced where the first and second tuft blocks are located in other manners such as being side by side in either a longitudinal or transverse direction with respect to the longitudinal axis of head 14 and neck 12. The concentric mounting of the tuft blocks is preferred since it would enable a more simplified drive arrangement to be used such as illustrated in FIG. 3 while minimizing space requirements. The invention, however, might be practiced where, for example, the first tuft block 16 is of a full or closed circular shape rather than being of ring-like shape and is mounted longitudinally adjacent to the second tuft block 18. The counter-oscillation could still be achieved by spacing the arms 34 and 36 of the spindle 32 a greater distance from each other. Alternatively, the tuft blocks 16,18 could be side by side and could be driven by separate drive mechanisms having, for example, separate shafts. Such separate drive mechanisms could also be used where the first tuft block 16 and the second tuft block 18 are mounted concentric to each other. The separate drive arrangements is not as preferred since it would require additional components and space requirements.

A characteristic of the invention is the provision of a third tuft block 38 which is illustrated as being between the neck 12 and the counter-oscillating tuft blocks 16, 18. It is to be understood, however, that the third tuft block could be located distally of the counteroscillating tuft blocks or laterally side by side to the counter-oscillating tuft blocks or between the counter-oscillating tuft blocks such as by being a separate coarcuate section within inner second tuft block 18 by making the second tuft block 18 of ring-like shape. It is preferred, however, that the third tuft block 38 be longitudinally outside of the counter-oscillating tuft blocks so as to extend the length of the surface area in head 14 having bristles.

The provision of three tuft blocks is also advantageous in that the powered toothbrush simulates, in appearance of the head, the structure of a conventional manual toothbrush which would make the powered or electric toothbrush more acceptable to users since the appearance simulates what a user is accustomed to seeing. In addition, the three sections enhance the efficiency of the toothbrush, both as a result of the movement of the tuft blocks and of the ability to readily retain toothpaste.

Figure 1:
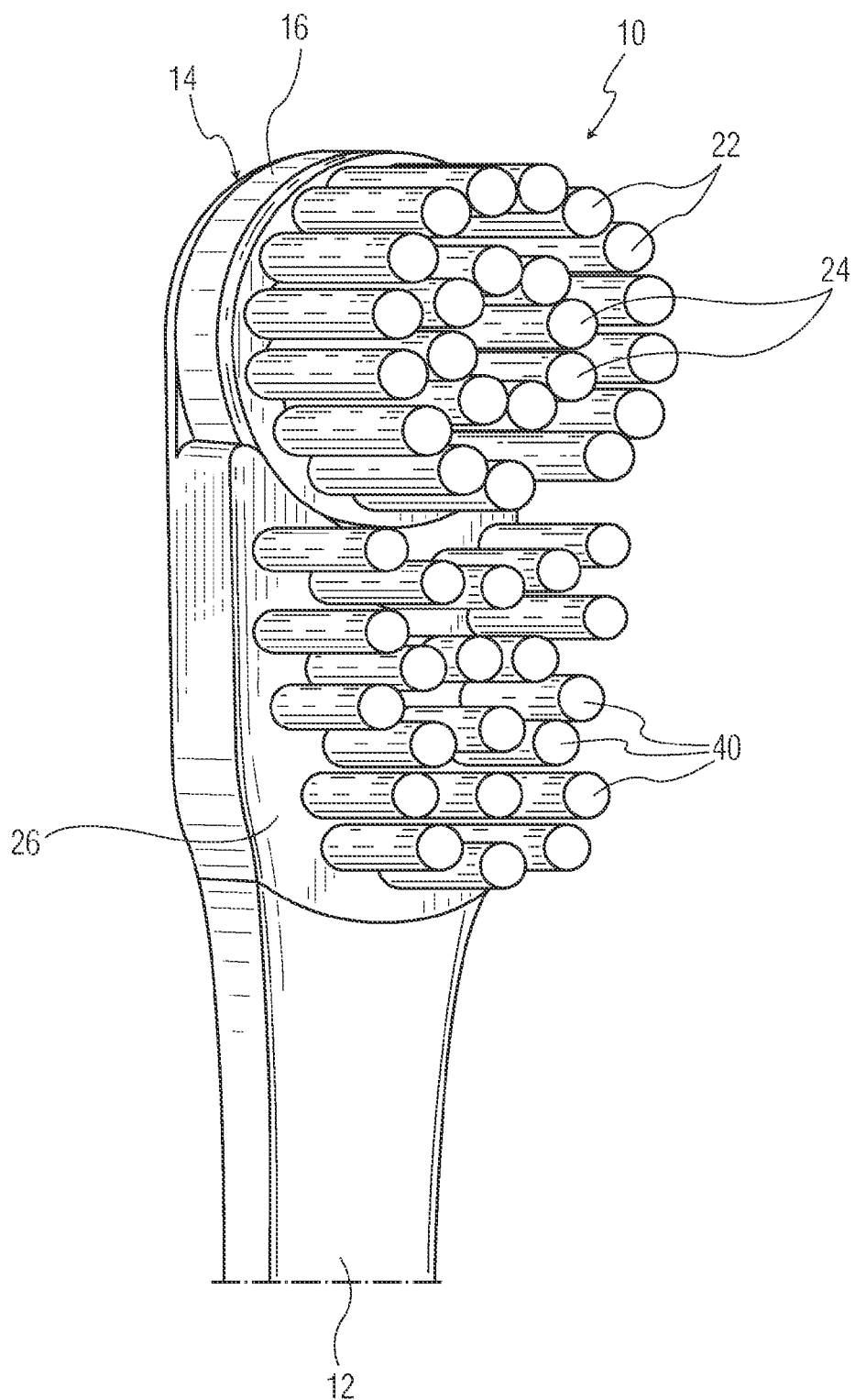
FIG. 1 is a perspective view of a toothbrush head in accordance with this invention.

As illustrated in FIGS. 1-3, third tuft block 38 is also provided with bristles 40 which extend outwardly from the outer surface 26 of third tuft block 38. The outer surface 26 of third tuft block 38 and the outer surface 26 of the inner and outer counter-oscillating tuft block 16,18 are preferably coplanar with each other so that the outer surface of the entire head is in a single plane. The invention, however, could be practiced wherein the third tuft block 38 contains alternating rows of the same height or where some or all of the rows of bristles extend outwardly a different distance than other rows of bristles to result in different stepped effects for the outer surface of the third tuft block 38.

In the illustrated embodiment as best shown in FIG. 3 at least some of the bristles 40 extend outwardly from the outer surface 26 of head 14 the same distance as bristles 22 so as to create a generally flat surface for receiving the toothpaste. Some of the bristles 41, however, may also be shorter as illustrated in FIG. 3.

While FIGS. 1-4 illustrate the bristles to be of conventional fiber form, the term "bristles" is intended to be used in a generic sense as cleaning elements or massage elements and could include, for example, elastomeric fingers or walls arranged in a circular cross-section shape or any type of desired shape, including straight portions or sinusoidal portions.

The bristles could be mounted to the tuft blocks or sections by extending through suitable openings in the tuft block so that the base of the bristles is mounted within or below the tuft block. If desired, the bristles could be embedded in an elastomeric material which would permit the bristles to have an independent motion in addition to the motion imparted by the oscillating tuft blocks 16 and 18, instead of being fixed bristles on fixed third section 38. Such various forms of bristles may thus be used for the bristles referred to or any of the sections of the head 14.

It is to be understood that the specific illustration of the bristles is merely for exemplary purposes. The invention can, however, be practiced with various combinations of the same or different bristle configurations secured to the head by known technology including such as staple technology, inmold tufting technology etc., and/or with the same or different bristle materials (such as nylon bristles, spiral bristles, rubber bristles, etc.) As previously mentioned, while FIGS. 1-4 illustrate the bristles to be generally perpendicular to the outer surface of head 14, some or all of the bristles may be angled at various angles with respect to the outer surface of the bristle head. It is thereby possible to select the combination of bristle configurations, bristle materials and bristle orientations to achieve specific intended results, such as to create as much movement from the oscillating tuft heads to deliver additional oral health benefits like enhanced cleaning, tooth polishing, tooth whitening and/or massaging of the gums.

It is to be understood that the invention can be practiced by locating tufts of bristles in any otherwise open area of the toothbrush head. Such tufts of bristles could be fixed bristles perpendicularly mounted or mounted at an angle to the exposed outer surface 26 of the head 14 or could be bristles mounted on an elastomeric base so as to be independently movable when pressure is applied. Such bristles in their normal condition could be either perpendicular or at an angle to the exposed outer surface of the toothbrush head.

The invention may also be practiced where different sets of bristles have different colors. Thus, for example, the arcuate row of bristles 22 could have a white color while the inner row of bristles 24 could have a blue color. The closed arcuate row of 8 bristles 40 at the portion of fixed section 38 adjacent to neck 12 and the tuft of bristles within that arcuate row could also be of a blue color while the next arcuate row of five tufts of bristles 41 could be of a white color and could be shorter than the remaining bristles on fixed section 38. The final seven tufts of bristles 40 adjacent to the counter-oscillating bristles could be of a green color. It is to be understood that the above description of specific color combinations is simply for exemplary purposes and any combination of colors including only one color could be used.

Preferably, fixed section 38 is of a saddle type construction to snap onto the head 14 in any suitable manner. As a result, it is possible to replace one fixed section having one type of bristles with another fixed section having different types of bristles.

Preferably, the invention is practiced where the third section 38 is a fixed section either having fixed bristles or bristles which can move independently of each other by being mounted on an elastomeric base. The invention, however, may also be practiced where the third section 38 is also movable. For example, the third section 38 may move in and out in a direction generally perpendicular to the outer surface 26 of head 14. This would result in a vibrating section. Any suitable drive mechanism may be used to accomplish this in and out vibrating motion such as the type of drive section described in U.S. Pat. No. Re. 35,941, all of the details of which are incorporated herein by reference thereto. Alternatively the vibrating section could be free floating without a positive drive. The resulting in and out motion is indicated by the arrow 42 in FIG. 3. Other forms of movement of third section 38 could be as indicated by the arrow 44 in FIG. 2 where the movement is longitudinal with respect to the longitudinal axis of head 14 or could be lateral as indicated by the arrow 46 of FIG. 2. Any suitable drive mechanism may be used to accomplish these motions which would be in a plane generally parallel to the outer surface 26 of head 14. Reference is made to copending application Ser. No. 10/066,459, filed Jan. 31, 2002 all of the details of which are incorporated herein by reference thereto.

As is apparent the invention thereby includes a first tuft block and a second tuft block which are mounted for counter-oscillation with respect to each other in a plane generally parallel to the outer surface of the head. In addition, the head of the toothbrush includes a third tuft block. The third tuft block may be a fixed section having fixed bristles or bristles independently movable by being mounted on an elastomeric base. Alternatively, the third tuft block may also move either laterally, transversely or in and out. The bristles on the various tuft blocks may be of any of the constructions previously described and may be of various lengths, colors and stiffness and may be mounted perpendicularly to or at an angle to the outer surface of the head.

What is claimed is:

1. A powered toothbrush comprising:
   a handle;
   a head mounted to one end of said handle, said head having an exposed outer surface and defining a longitudinal axis;
   a first tuft block mounted to said head, said first tuft block having bristles extending outwardly from said outer surface;
   a second tuft block mounted to said head, said second tuft block having bristles extending outwardly from said outer surface;
   a drive structure for oscillating each of said first and said second tuft blocks in counter rotational direction within a plane generally parallel to said outer surface; and
   a third tuft block having bristles extending outwardly from said outer surface, said third tuft block being mounted to said head separate from said first and second tuft blocks and located substantially between said handle and said first and second tuft blocks without being rotationally movable in a plane generally parallel to said exposed surface;
   wherein said third tuft block is movably mounted on said head and is movable in a longitudinal direction in a plane generally parallel to said outer surface; and
   wherein said bristles of said first tuft block and said bristles of said second tuft block define a pair of concentric circles of bristles that form a cup-like structure that includes an outer circle of bristles rotatable in a first direction and an inner circle of bristles rotatable in an opposing second direction.

2. The toothbrush of claim 1 wherein at least some of said bristles on said first tuft block, said second tuft block and said third tuft block are embedded in an elastomeric material for independent motion about their mounting.

* * * * *